United States Patent [19]
Dinh et al.

[11] Patent Number: 6,042,578
[45] Date of Patent: *Mar. 28, 2000

[54] CATHETER REINFORCING BRAIDS

[75] Inventors: John S. Dinh, Maple Grove; Thomas E. Eibs, St. Louis Park; Alex A. Peterson, Maple Grove; John B. Logan, Plymouth, all of Minn.; Mukund R. Patel, San Jose, Calif.; William F. Polley, Mound, Minn.

[73] Assignee: Schneider (USA) Inc., Maple Grove, Minn.

[ * ] Notice: This patent is subject to a terminal disclaimer.

[21] Appl. No.: 08/833,639

[22] Filed: Apr. 8, 1997

Related U.S. Application Data

[63] Continuation-in-part of application No. 08/645,381, May 13, 1996, abandoned.

[51] Int. Cl.[7] .................................................. A61M 25/00
[52] U.S. Cl. ............................................ 604/527; 604/524
[58] Field of Search ................................... 604/280, 282, 604/264, 265, 524, 526, 527, 529, 532

[56] References Cited

U.S. PATENT DOCUMENTS

| | | | |
|---|---|---|---|
| 4,531,943 | 7/1985 | Van Tassel et al. | 604/280 |
| 4,646,742 | 3/1987 | Packard et al. | 128/344 |
| 4,898,591 | 2/1990 | Jang et al. | 604/282 |
| 4,994,032 | 2/1991 | Sugiyama et al. . | |
| 4,998,923 | 3/1991 | Samson et al. | 606/194 |
| 5,035,694 | 7/1991 | Kasprzyk et al. | 606/27 |
| 5,176,661 | 1/1993 | Evard et al. | 604/282 |
| 5,180,376 | 1/1993 | Fischell . | |
| 5,201,757 | 4/1993 | Heyn et al. | 606/198 |
| 5,221,270 | 6/1993 | Parker | 604/282 |
| 5,248,305 | 9/1993 | Zdrahala . | |
| 5,256,144 | 10/1993 | Kraus et al. | 604/96 |
| 5,312,356 | 5/1994 | Engelson et al. | 604/164 |
| 5,342,383 | 8/1994 | Thomas . | |
| 5,357,955 | 10/1994 | Wolf et al. | 128/634 |
| 5,387,199 | 2/1995 | Siman et al. | 604/282 |
| 5,403,292 | 4/1995 | Ju . | |
| 5,451,209 | 9/1995 | Ainsworth et al. | 604/96 |
| 5,496,291 | 3/1996 | Spencer | 604/280 |
| 5,514,236 | 5/1996 | Avellanet et al. . | |
| 5,522,832 | 6/1996 | Kugo et al. . | |
| 5,527,325 | 6/1996 | Conley et al. . | |

(List continued on next page.)

FOREIGN PATENT DOCUMENTS

| | | |
|---|---|---|
| 0520692A1 | 12/1992 | European Pat. Off. . |
| 93/08986 | 5/1993 | WIPO . |
| 9601664 | 1/1996 | WIPO . |
| 9737713 | 10/1997 | WIPO . |

OTHER PUBLICATIONS

Definition of polytetrafluoroethylene from Hawley's Condensed Chemical Dicitonary, Twelfth Edition, Revised by Richard J. Lewis, Sr., p. 942, 1993.

Search Report dated Sep. 29, 1997 in corresponding European Patent Application No. 97201366.8, together with Communication, Supplementary Sheet B (1 page), and two–page Annex.

"Declaration of Thomas E. Eibs in Support of Supplemental Information Disclosure Statement," dated Sep. 9, 1996. (The original Declaration is on file in parent application serial No. 08/645,381.).

Search Report dated Jan. 16, 1998 in corresponding European Patent Application No. 97201366.8, together with Communication and two–page Annex.

*Primary Examiner*—Wynn Wood Coggins
*Assistant Examiner*—Deborah Blyveis
*Attorney, Agent, or Firm*—Crompton, Seager & Tufte, LLC

[57] ABSTRACT

An intravascular catheter having an elongated tubular body with a proximal portion, a distal portion and a lumen extending therebetween. The tubular body is formed with polymeric materials, preferably containing no radiopaque filler, and metallic reinforcing braiding configured to provide the catheter with radiopaque properties and/or kink resistance.

19 Claims, 8 Drawing Sheets

U.S. PATENT DOCUMENTS

| | | | |
|---|---|---|---|
| 5,531,719 | 7/1996 | Takahashi . | |
| 5,533,987 | 7/1996 | Pray et al. . | |
| 5,538,513 | 7/1996 | Okajima . | |
| 5,545,151 | 8/1996 | O'Connor et al. . | |
| 5,565,523 | 10/1996 | Chen et al. . | |
| 5,569,200 | 10/1996 | Umeno et al. | 604/96 |
| 5,569,220 | 10/1996 | Webster, Jr. | 604/282 |
| 5,569,221 | 10/1996 | Houser et al. | 604/282 |
| 5,573,520 | 11/1996 | Schwartz et al. . | |
| 5,573,522 | 11/1996 | Houser et al. | 604/282 |
| 5,599,325 | 2/1997 | Ju et al. . | |
| 5,695,468 | 12/1997 | Lafontaine et al. . | |
| 5,725,513 | 3/1998 | Ju et al. | 604/280 |
| 5,728,063 | 3/1998 | Preissman et al. . | |
| 5,741,333 | 4/1998 | Frid | 623/12 |
| 5,755,704 | 5/1998 | Lunn | 604/282- |

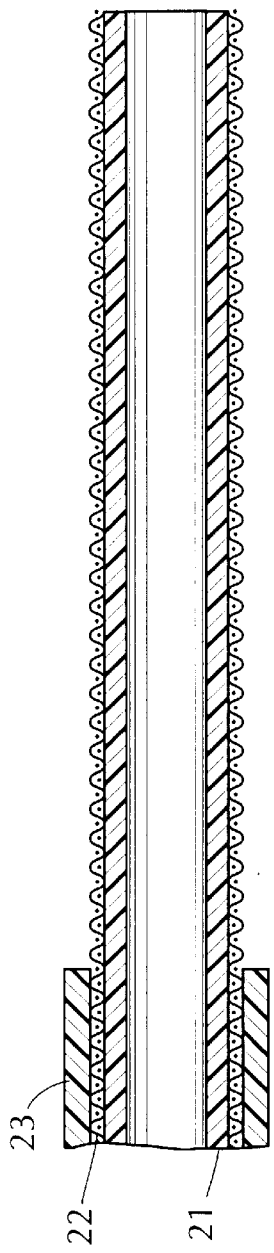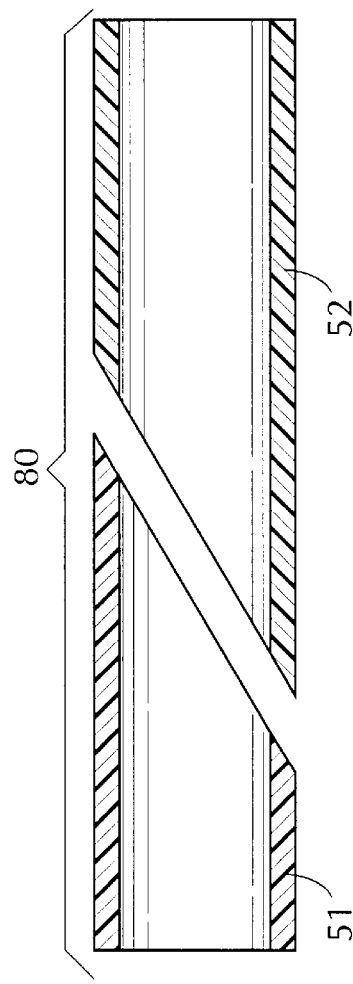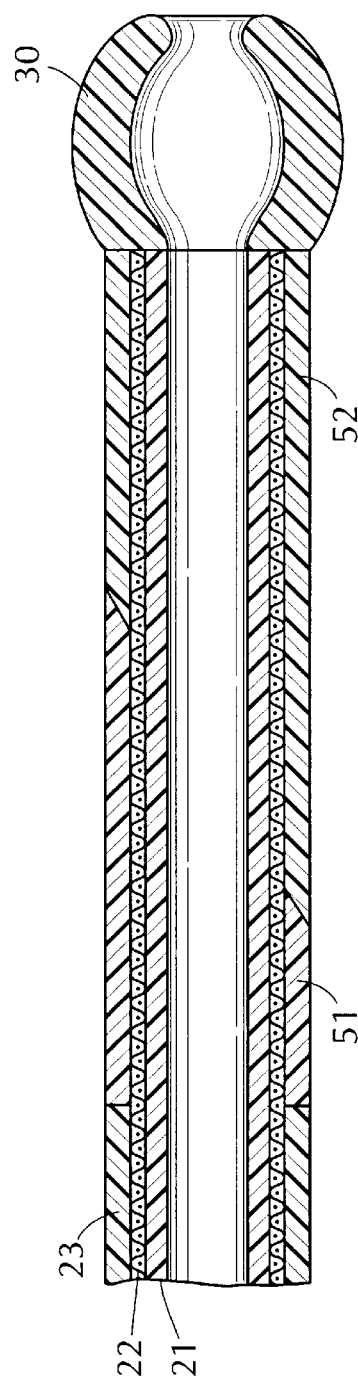

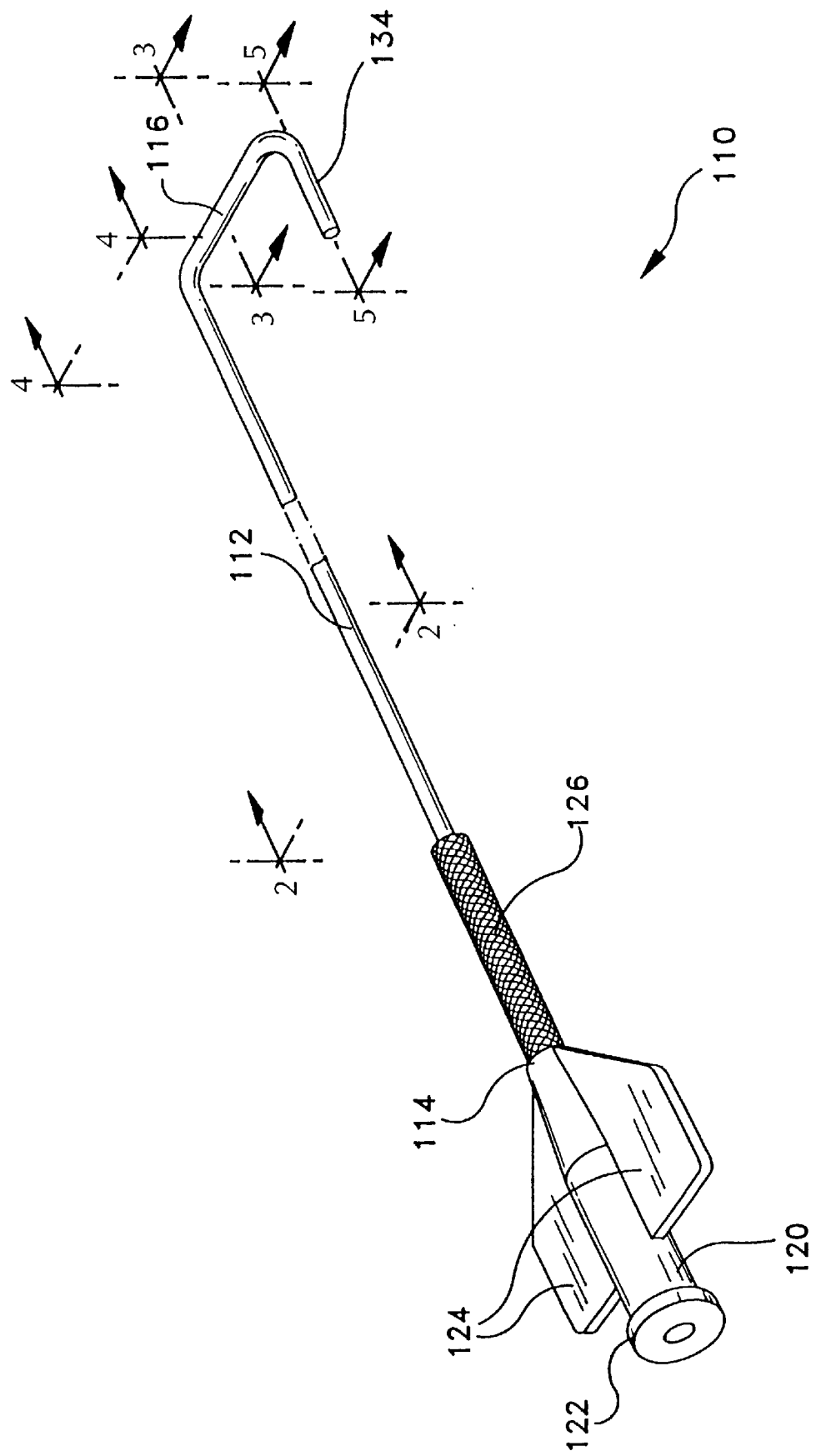

CATHETER REINFORCING BRAIDS

This application is a continuation-in-part of U.S. patent application Ser. No. 08/645,381, filed May 13, 1996 now abandoned.

BACKGROUND OF THE INVENTION

The present invention relates to intravascular catheters, and more particularly to a catheter having metallic reinforcing braiding configured to provide the catheter with radiopaque properties and/or kink resistance.

Several types of catheters are utilized for intravascular treatment. Examples of intravascular catheters include guide catheters, angioplasty catheters, stent delivery devices, angiographic catheters, neuro catheters, and the like.

Guiding catheters are commonly used during coronary angioplasty procedures to aid in delivering a balloon catheter or other interventional medical devices to a treatment site in a coronary vessel. In a routine coronary angioplasty procedure, a guiding catheter is introduced into a peripheral artery and advanced over a guidewire through the aorta until the distal end of the guiding catheter is engaged with the appropriate coronary ostium. Next a balloon dilatation catheter is introduced over the guidewire and through the guiding catheter. The guidewire is advanced past the distal end of the guiding catheter within the lumen of the diseased vessel and manipulated across the region of the stenosis. The balloon dilatation catheter is then advanced past the distal end of the guiding catheter over the guidewire until the balloon is positioned across the stenotic lesion. After the balloon is inflated to dilate the blood vessel in the region of the stenotic lesion, the guidewire, balloon dilatation catheter and guiding catheter are withdrawn.

Guiding catheters typically have preformed bends formed along their distal portion to facilitate placement of the distal end of the guiding catheter into the ostium of a particular coronary artery of a patient. In order to function efficiently, guiding catheters should have a relatively stiff main body portion and soft distal tip. The stiff main body portion gives the guiding catheter sufficient "pushability" and "torqueability" to allow the guiding catheter to be inserted percutaneously into a peripheral artery, moved and rotated in the vasculature to position the distal end of the catheter at the desired site adjacent to a particular coronary artery. However, the distal portion should have sufficient flexibility so that it can track over a guidewire and be maneuvered through a tortuous path to the treatment site. In addition, a soft distal tip at the very distal end of the catheter should be used to minimize the risk of causing trauma to a blood vessel while the guiding catheter is being moved through the vasculature to the proper position. Such a soft tip is described in U.S. Pat. No. 4,531,943. In additon, the inner surface of the guiding catheter should be lubricious to facilitate movement of guidewires, balloon catheters and other interventional medical devices therethrough.

Angiographic catheters can be used in evaluating the progress of coronary artery disease in patients. Angiography procedures are used to view the patency of selected blood vessels. In carrying out this procedure, a diagnostic catheter having a desired distal end curvature configuration may be advanced over a guide wire through the vascular system of the patient until the distal end of the catheter is steered into the particular coronary artery to be examined.

A non-limiting example of an angioplasty catheter is found in U.S. Pat. No. 4,646,742. A non-limiting example of a stent deployment device is found in U.S. Pat. No. 5,201,757.

In that the path taken by intravascular catheters is sometimes tortuous, it is important that an intravascular catheter can be steered by torquing its proximal hub and that the torque be transmitted to the distal end in a smooth, controllable fashion. Moreover, the catheter should have sufficient strength in the longitudinal direction so as not to kink or fold as it is advanced through the vascular system. It should also possess a lubricious core lumen to facilitate passage of a guidewire or possibly another catheter or device therethrough.

It is also a desirable feature of certain intravascular catheters that it possess a relatively large lumen to allow fluids, such as radiopaque contrast fluid to be injected therethrough and out the distal end so that the area of the vascular system under investigation can be viewed fluoroscopically.

It is also a desirable feature of certain intravascular catheters that it possess radiopaque and/or kink resistance qualities.

The desirable properties of a catheter having a relatively small O.D. and a relatively large I.D. dictates a relatively thin wall. To maintain the desired torqueability and pushability characteristics of a thin wall catheter calls for considerable ingenuity in the formulation of the materials employed and the constructional techniques utilized.

SUMMARY OF THE INVENTION

In accordance with the present invention there is provided an intravascular catheter with an elongated tubular body having a proximal portion, a distal portion and a lumen extending therebetween. The tubular body has a first layer defining the lumen, the first layer made of a polymer having a coefficient of friction of less than about 0.50; a second layer disposed about the first layer, the second layer made of a polymer selected from polyetherester elastomer, polybutylene terephthalate, and combinations thereof; and a reinforcing means. The first layer may be a polymer selected from polytetrafluoroethylene, polyvinylidene fluoride, and polyamide, and may be a polymer having a kinetic coefficient of friction (steel on polymer) less than about 0.35, and preferably less than about 0.10. The first layer may consist essentially of polytetrafluoroethylene. The second layer may have a durometer of from about 30D –90D, and may be from about 38D –74D. In one embodiment, the second layer will preferably be about 30D at the distal end of the bodystock and about 90D at the proximal end of the bodystock. The second layer may be polyetherester blended with polybutylene terephthalate such as about 10–94 weight percent polybutylene terephthalate. The second layer may be about 8–12 weight percent polyetherester and about 88–92 weight percent polybutylene terephthalate. The reinforcing means may be totally embedded between the first layer and the second layer, or substantially embedded in the second layer. The reinforcing means may be a braided metal mesh of filaments extending from the proximal portion of the tubular body toward the distal portion of the tubular body by a predetermined distance. The reinforcing means may extend to the distal portion of the catheter. The braided metal mesh may be metal filaments braided in a 1 over 1 pattern or 2 over 2 configuration, and may be made of filaments formed of a metal selected from stainless steel and ELGILOY nickel-cobalt alloy. The reinforcing means may be a polymer forming a mesh, a tube, or a fabric, and the polymer may be carbon fibers or polyaramide. The intravascular catheter may have an annular soft-tip member bonded to the distal end of the tubular body member, and the soft-tip member may be polyetherester elastomer having a durometer less than about 50D. The intravascular catheter may have an outer diameter in the range of from about 2 French to 24 French, preferably from about 4 French to about 12 French.

In another embodiment of the present invention, the present invention relates to a guide catheter having an elongate tubular body with a proximal portion, a distal portion and a lumen extending therebetween. The tubular body has an outside diameter of from about 4 French to about 12 French and has a first layer forming the lumen and made of polytetrafluoroethylene; a braided metal mesh of filaments at least partially surrounding the inner layer; and a second layer at least partially covering the reinforcing means, the second layer made of a blend of polyetherester elastomer and polybutylene terephthalate. The second layer may have a durometer of from about 38D –74D, and may be made of about 10–94 weight percent polybutylene terephthalate. In one embodiment, the second layer will preferably be about 30D at the distal end of the bodystock and about 90D at the proximal end of the bodystock. The second layer will preferably be made of about 8–12 weight percent polyetherester and about 88–92 weight percent polybutylene terephthalate. The braided metal mesh may be made of metal filaments braided in a 1 over 1 pattern or 2 over 2 configuration. The intravascular catheter may further include an annular soft-tip member bonded to the distal end of the tubular body member, and the soft-tip member may comprise polyetherester elastomer having a durometer less than about 50D.

In another embodiment of the present invention, the present invention relates to an intravascular catheter having an elongate tubular body having a proximal portion, a distal portion and a lumen extending therebetween. The tubular body may be made of: (a) polymeric material containing substantially no radiopaque filler; and (b) metallic reinforcing braiding configured with sufficient effective thickness to provide the elongate tubular body with substantial radiopacity. The polymeric material may be a polymer selected from polyetherester elastomer, polybutylene terephthalate, and combinations thereof. The metallic reinforcing braiding may be configured in a one-over-one paired wire construction.

In yet another embodiment of the present invention, an intravascular catheter has an elongate tubular body with a proximal portion, a distal portion and a lumen extending therebetween, and the tubular body is made of: (a) polymeric material containing substantially no radiopaque filler; and (b) metallic reinforcing braiding, wherein the combination of polymeric material comprising substantially no radiopaque filler and metallic braid has an amount of radiopacity which is greater than or equal to the amount of radiopacity which would result from a catheter without metallic reinforcing consisting of polymeric material loaded with 20% barium sulfate, preferably greater than about 30%, more preferably between about 30–40%.

DESCRIPTION OF THE DRAWINGS

The foregoing features, objects and advantages of the invention will become apparent to those skilled in the art from the following detailed description of certain preferred embodiments especially when considered in conjunction with the accompanying drawings in which like numerals in the several views refer to corresponding parts. These figures are provided to illustrate, and not limit, the present invention.

FIG. 2 is a longitudinal sectional view of the distal portion of one embodiment of the guiding catheter of this invention prior to the attachment of the stem and tip;

FIG. 3 is a longitudinal sectional view of the stem transition sleeve and stem sleeve prior to assembly of the guiding catheter of this invention;

FIG. 4 is a longitudinal sectional view of the distal portion of one embodiment of the guiding catheter of this invention;

FIG. 6 is a perspective view of a diagnostic catheter constructed in accordance with the present invention;

DESCRIPTION OF THE PREFERRED EMBODIMENTS

Figure 1:
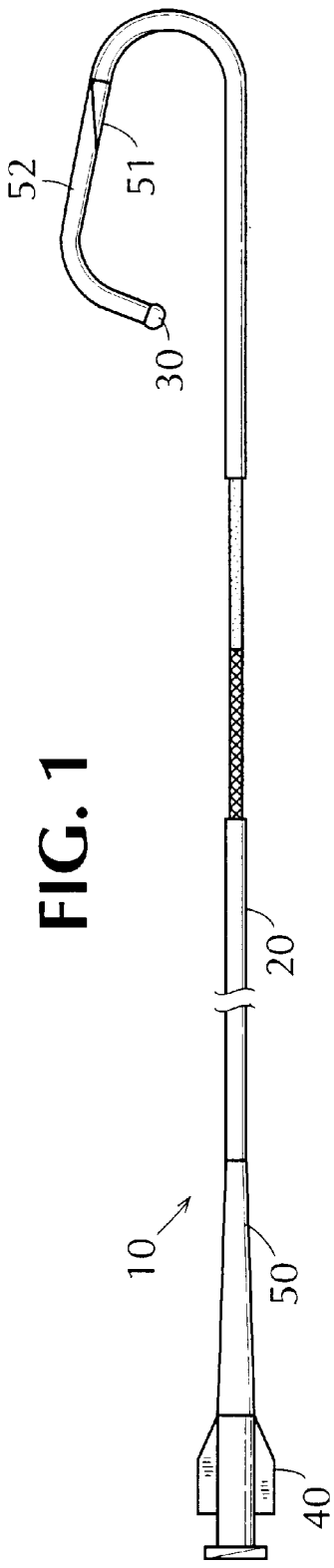
FIG. 1 is a plan view of one embodiment of the guiding catheter of this invention with a portion of the catheter removed to show the construction of the bodystock.
Figure 5:
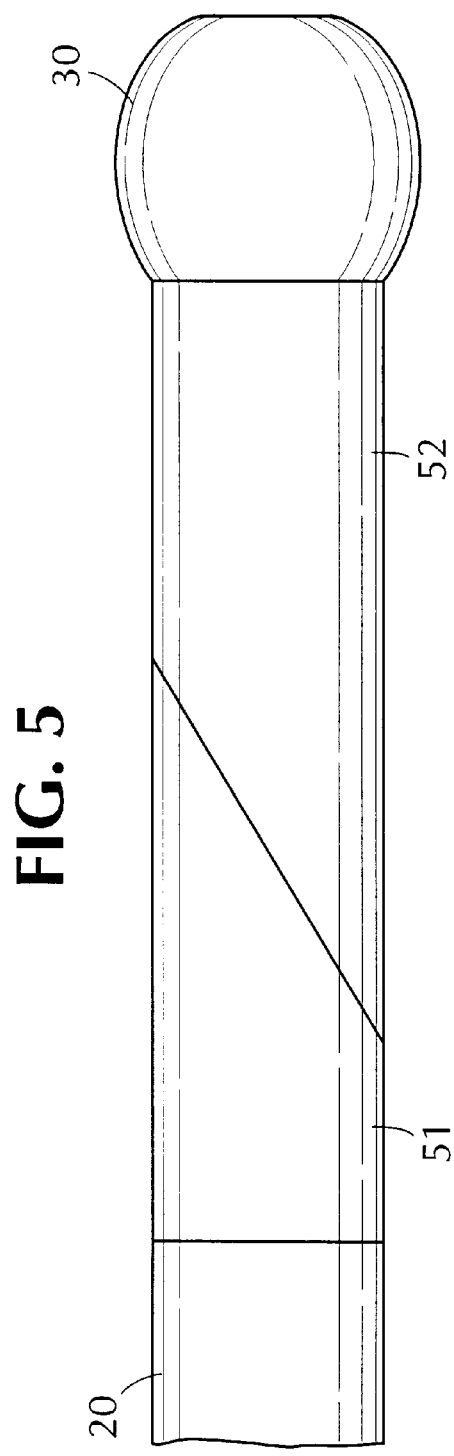
FIG. 5 is a plan view of the distal portion of the guiding catheter of this invention showing the stem transition sleeve, stem sleeve and soft tip.

One embodiment of the invention is a guiding catheter 10 which has a tubular bodystock 20 and a soft tip 30 attached to the distal end of bodystock 20. Guiding catheter 10 can have any desired inner diameter and outer diameter. Typical dimensions are an inner diameter of between about 0.050 inches to about 0.130 inches (0.127 cm to 0.330 cm) and an outer diameter of about 0.070 inches to about 0.150 inches (0.178 cm to 0.381 cm). A conventional polycarbonate hub 40 is attached to the proximal end of bodystock 20. In addition, an extruded strain relief tube 50 is connected to hub 40 and the proximal portion of bodystock 20. Strain relief tube 50 preferably may have a tapered design as shown in FIG. 1. However, a constant outside diameter construction could also be used.

Bodystock 20 is formed from an inner liner 21, an intermediate wire mesh braid 22 and an outer jacket 23. Inner liner 21 is formed from a polymer having a coefficient of friction of less than about 0.50, preferably polytetrafluoroethylene. Suitable polytetrafluoroethylene can be purchased on the open market. The polytetrafluoroethylene preferably has a thickness of between about 0.0010 inches (0.0025 cm) and about 0.0050 inches (0.0127 cm).

Inner liner 21 when formed from a polymer having a coefficient of friction of less than 0.50 provides a lubricious surface facing the lumen of guiding catheter 10. This facilitates the passage of other medical devices therethrough.

Metallic reinforcing braid 22 is formed from, e.g., stainless steel wires disposed over inner liner 21. Although stainless steel wire is preferred, other suitable materials such as ELGILOY nickel-cobalt alloy could also be used. The stainless steel wire may have a circular cross-section with a diameter of between about 0.0010 inches (0.0025 cm) and about 0.0050 inches (0.0127 cm), preferably about 0.003 inches (0.008 cm). Alternatively, a flat wire could be used. The metallic reinforcing braid 22 is described in more detail below.

Outer jacket 23 is formed from a blend of polyetherester elastomer and polybutylene terephthalate (PBT). Suitable polyetherester elastomer and polybutylene terephthalate (PBT) can be purchased on the open market. Outer jacket 23 may have a durometer of between about 38D and about 74D. In one embodiment, the second layer will preferably be about 30D at the distal end of the bodystock and about 90D at the proximal end of the bodystock. The use of a polyetherester elastomer/PBT blend provides a bodystock material that is sufficiently stiff so that guiding catheter 10 has a proximal portion with enhanced "pushability" and "torqueability".

Preferably, the polymeric material for outer jacket 23 and inner liner 21 will contain substantially no radiopaque fillers such as barium sulfate, bismuth subcarbonate, bismuth trioxide and bismuth oxychloride. Preferably the outer jacket 23 and/or inner liner 21 will contain less than 5 weight percent radiopaque filler, more preferably less than 1 weight percent, even more preferably less than 0.5 weight percent, and most preferably 0 weight percent. A pigment can be used to color outer jacket 23. If such a pigment is used, preferably about 0.05 to about 0.5% by weight is used. Lesser or greater amounts of the pigment can be used depending on the color desired.

Soft tip 30 constitutes the most distal end of guiding catheter 10. It is formed from polyetherester elastomer. Preferably soft tip 30 has a durometer of between about 25D and about 50D. This gives soft tip 30 a softness that is sufficient to minimize the chances of damage to the inner surface of a blood vessel through which a guiding catheter 10 may pass. In addition, it is hard enough to maintain an opening therethrough to allow the passage of a guidewire, balloon catheter or other interventional medical devices to pass out of the distal end of soft tip 30. Soft tip 30 can be made radiopaque by mixing, e.g., 15–50% by weight barium sulfate with the polyetherester elastomer. Of course greater or lesser amounts of barium sulfate or other radiopaque filler can be used. A 4% by weight loading of titanium dioxide can be used to color soft tip 30. Again greater or lesser amounts of titanium dioxide can be used. Preferably soft tip 30 has a length of between about 0.04 inches (0.10 cm) to about 0.20 (0.51 cm) inches.

Guiding catheter 10 may have a stem 80 located between bodystock 20 and soft tip 30. Stem 80 is composed of stem transition sleeve 51 and a stem sleeve 52. Stem transition sleeve 51 is formed from 38D to 55D polyetherester elastomer. It will preferably contain no radiopaque fillers such as barium sulfate. Organic pigment can be used. Stem sleeve 52 is formed from 38D to 55D polyetherester elastomer. It will preferably contain no radiopaque fillers such as barium sulfate. 4% by weight of titanium dioxide or 0.4% by weight of an organic pigment can be used to provide color to stem sleeve 52.

Stem transition sleeve 51 has a taper along the distal portion. This taper as shown is about 20 degrees but can generally be from about 0 degrees to about 30 degrees. Stem sleeve 52 has a complementary taper along its proximal portion to provide a smooth transition between stem transition sleeve 51 and stem sleeve 52. The length of stem sleeve 52 can vary depending on the length of the distal portion of guiding catheter 10 that is desired to be flexible. Stem sleeve 52 may be from about 0.45 inches (1.14 cm) to about 2.1 inches (5.33 cm) as measured from its most distal end to the most proximal end of the taper. In addition, stem 80 can have a total length of between about 0.5 inches (1.27 cm) to about 6 inches (15.24 cm).

Stem transition sleeve 51 and stem sleeve 52 fit over the distal portion of bodystock 20. This configuration provides a smooth transition in the flexibility of guiding catheter 10 from its proximal end to its distal end. This smooth transition from the high hardness/stiffness of bodystock 20 to the high softness of soft tip 30 eliminates stress concentration at the stem to bodystock joint. High stress concentrations at this joint would promote kinking and failure of guiding catheter 10.

Guiding catheter 10 can be manufactured according to the following process.

Step A

1. Clean a weld mandrel with alcohol and lint free cloth.
2. Slide mandrel 90% into an etched PTFE tube. Tie a knot about ½ inch from the end of the PTFE tube, and slide the weld mandrel the rest of the way into the PTFE. Trim excess PTFE outside of the knot.
3. Cut braided metal stock to a desired length. Slide the braid stock into an assembly tube. Remove and dispose of the braid core rod while holding the free end of the braid assembly with other hand. This leaves the unsupported braid inside the assembly tube. Slide the end of the PTFE/mandrel assembly (knot end first) into the braid which is in the assembly tube. Remove the braid/PTFE/mandrel from the assembly tube. Snug and secure the braid down onto the PTFE by pulling it axially and twisting the free ends. Trim the twisted braid back to about ¼ inch beyond the end of the weld mandrel on both ends.
4. Cut a desired number of outer layer tubes, such as a first, second and third outer layer tubes, to desired lengths. Each tube may have different durometers. Make one slit in each first and second tube axially along their length. Tube three is not slit. Slide the three tubes onto the braid/PTFE/mandrel assembly. Move the tubes together until each is butted against the adjoining tube, but not overlapped. The three tubes should be approximately centered on the braid/PTFE/mandrel assembly. Slide a piece of the assembly heat shrink completely over the tubes/braid PTFE/mandrel assembly, until it is also centered on the tubes/braid/PTFE/mandrel assembly. Using a hot air source at about 200° F. to 400° F., shrink the assembly heat shrink in four places: both ends and above both tube butt joints.
5. Place heat shrink/tubes/braid/PTFE/mandrel assembly in pre-heated convection oven at a desired temperature for a desired time and then remove. The time shall begin when the oven temperature has recovered to within 10° F. of the specified temperature. During this process and during the subsequent cooldown after removal from the oven, nothing is to touch the assembly, except at the ends (where there are no tubes).
6. After the part has cooled to a comfortable touch, remove the heat shrink by slitting it axially over its length. Dispose of used heat shrink. Trim the twisted braid on one end of the assembly to expose the weld mandrel. Pull the weld mandrel out of the now fused tube/braid/PTFE assembly.
7. Trim both ends of the catheter to the specified length using a single edge razor blade and specified trim mandrel.

Step B
1. Set a defined time and temperature of a tip welding system.
2. Cut the tip tubes to the desired length. Place one tip tube on the tip weld mandrel, and slide it against the step. Cut tip heat shrink to a desired length, and slide it onto the catheter. Gently place the tip weld mandrel/tip tube assembly into the catheter until the end of the catheter butts against the tip tube, and then slide the heat shrink onto this assembly until it overlaps the tip tube completely.
3. Ensuring that no relative motion occurs between the pieces of the weld mandrel/tip tube/catheter/heat shrink assembly, place it in the proper location between the jaws of the tip welding fixture. Axial orientation is correct when the right end of the tip welding mandrel is approximately aligned with the right end of the jaws of the welder. Start the welding system when alignment is achieved.
4. When the welding cycle is complete and the part cool to the touch, remove the heat shrink. Push the catheter off from the mandrel by pushing against the distal end of the soft tip.
5. Visually inspect the catheter/soft tip weld area with a microscope for defects.
6. Mount a trimming pin into a small lathe. Mount a rolling tip trimming tool in a lathe tool mount. Place the end of the catheter onto the trimming pin the distance necessary to achieve the specified trim length. Turning the lathe at about 20 RPM, move the trimming tool into the part until the tip is trimmed off. Stop the lathe and remove the part and discard the trimmed piece.

Step C
1. Clean forming wires with 70:30 isopropyl alcohol/water.
2. Mount the catheter onto the forming wires until the distal tip is properly aligned on the forming wire.
3. Arrange the catheter/forming wire assemblies onto the oven tray in such a way that the soft tips are not in contact with anything other than the wire upon which they are mounted.
4. Place the tray into the forming oven at a desired temperature for a desired time.
5. After the parts have cooled, remove the forming wires and compare the shape to the specified shape template.

Step D
1. Slide a desired strain relief onto the proximal end of the catheter about 3 inches (7.6 cm). Apply a desired adhesive around the end of the catheter in a continuous bead, leaving the last 0.010 to 0.020 inches (0.25 to 0.051 cm) of catheter free of adhesive. Slide the catheter into the hub, rotate the hub about 1 turn and align the wings of the hub in approximately the same plane as the formed shape. Apply another small bead of the specified adhesive to the bodystock immediately adjacent to the hub, and slide the strain relief into the hub. Blot excess adhesive from the joint. Visually inspect the inside of the hub for excess glue.

FIGS. 6–12 relate to a diagnostic catheter of the present invention. Referring first to FIG. 6, there is indicated generally by numeral 110 a diagnostic catheter comprising the present invention. It includes an elongated tubular body 112 having a proximal end 114, a distal end 116 and a lumen 118 extending therebetween. Affixed to the proximal end 114 of the tubular body 112 is a molded plastic hub 120 having a Luer fitting 122 at its proximal end and flared wings 124 projecting radially from the diametrically opposed sides thereof to facilitate twisting of the catheter. An elastomeric sleeve 126 surrounds the proximal end portion of the tubular body 112 and functions as a strain relief member. The sleeve 126 is preferably roughened or knurled to facilitate gripping and rotation thereof using a three-finger catheter engagement. The length of the tubular body 112 will typically be 3½ to 4 feet (1.1 to 1.2 meters) in length and will have an outside diameter that is generally uniform over this length and will come in various sizes from, e.g., 3 Fr to 8 Fr.

Figure 7:
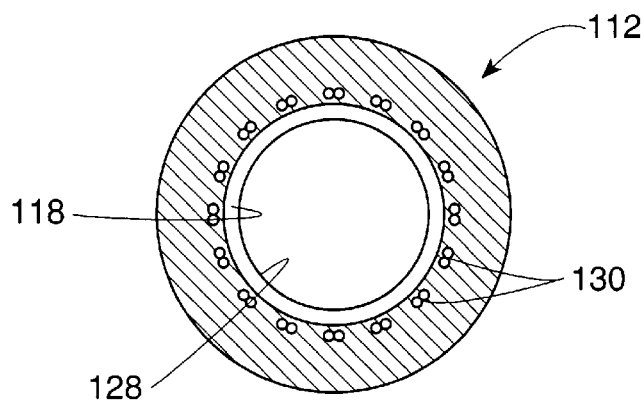
FIG. 7 is a cross-sectional view of the catheter of FIG. 6 taken along the line 2—2.
Figure 8:
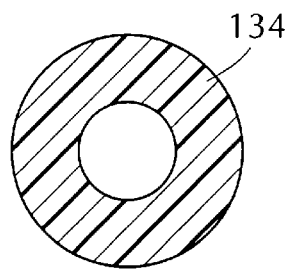
FIG. 8 is a cross-sectional view taken through the stem member of the catheter along the line 3—3 in FIG. 6.

Referring to the cross-sectional view of FIG. 7, it can be seen that the tubular body 112 is formed with an inner lubricious layer 128. With this material for the inner layer 128, the surface defining the lumen 118 is inherently lubricious. The inner layer 128 preferably has a wall thickness in the range of from 0.001 to 0.008 inches (0.0025 to 0.0203 cm) with 0.0025±0.0005 inches (0.0064±0.0127 cm) being preferred.

Figure 9:
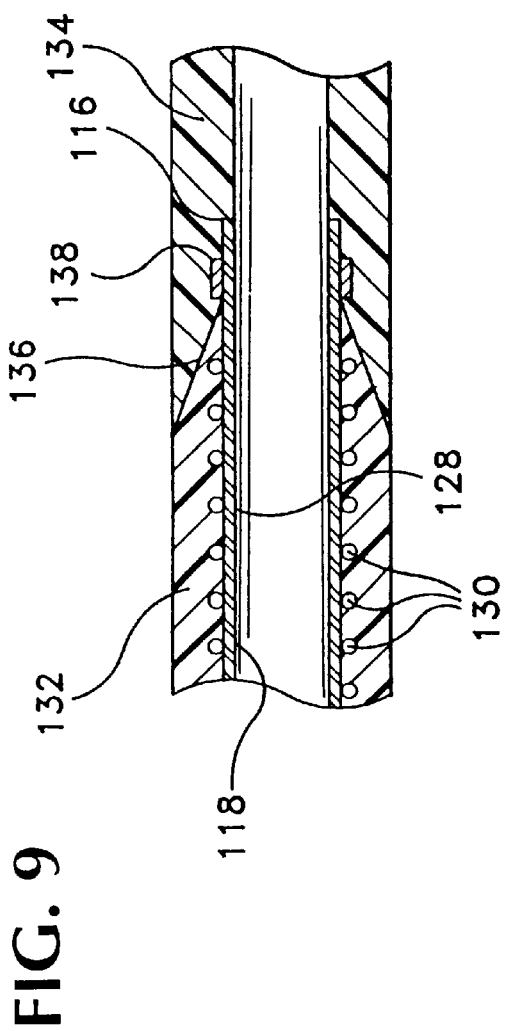
FIG. 9 is a longitudinal cross-sectional view taken along the line 4—4 which passes through the joint between the tubular body stock and the stem member.
Figure 10:
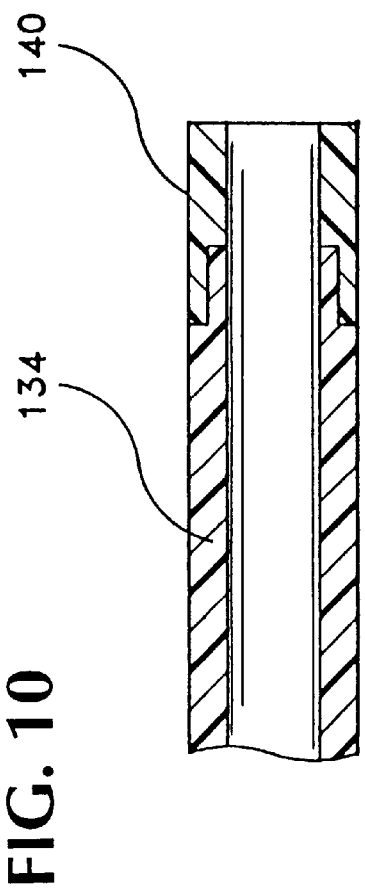
FIG. 10 is a longitudinal cross-sectional view taken through the distal end portion of the catheter along the line 5—5 in FIG. 6.
Figure 15:
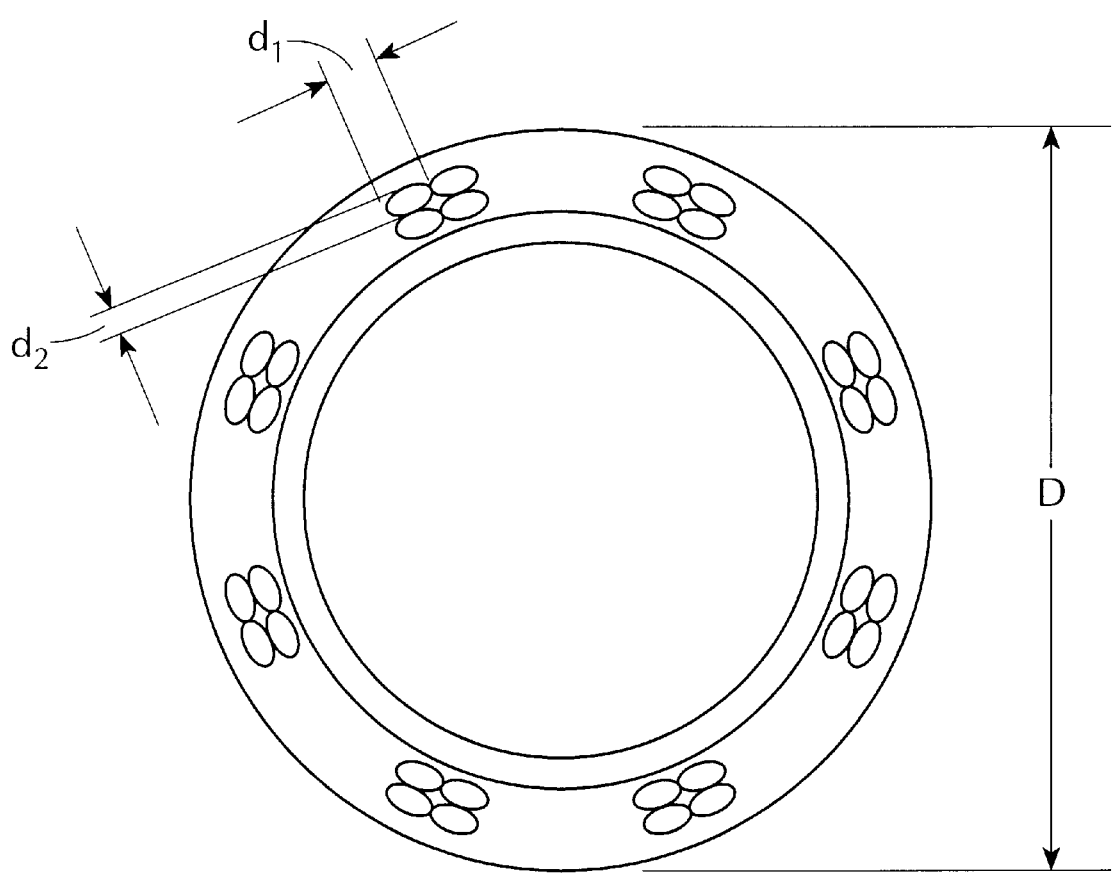
FIG. 15 shows a cross-section of a catheter in accordance with the present invention.

As can also be seen in the cross-sectional views of FIGS. 7 and 9, a reinforcing means, in this case a braided sleeve of metal wires 130 is disposed about the inner layer 128. As shown in FIG. 15, the cross-sectional view of the wires will generally be elliptical where the wires are braided and the filaments extend in a helix. The metallic reinforcing means 130 is described in more detail below.

Following placement of the reinforcing means, an outer layer 132 is disposed onto the assembly. The outer layer may comprise a blend of about 90 weight percent polyetherester and about 10 weight percent polybutylene terephthalate. As can be seen from the cross-sectional views of FIG. 9, the outer layer 132 may totally embed the reinforcing means 130. In certain embodiments, outer layer 132 substantially embeds reinforcing means 130, such that only minor portions of the reinforcing means 130 protrude from the outer layer 132. To provide a desired shape characteristic to the distal end portion of the diagnostic catheter, a tubular stem member 134 may be thermally bonded to the distal end portion of the braided tubular body 112. As is best seen in FIG. 9, the braided tubular body has its outer layer or jacket 132 ground to a bevel as at 136. By beveling the distal end portion 116 of the tubular body 112, greater surface area is provided for effecting attachment of the stem member 134. In that the grinding operation used to create the bevel reduces the thickness of the outer jacket relative to the ends of the wires 130 comprising the braided sleeve, a band or ring 138 of a non-penetrable material may be used to surround the free ends of the braid wires. Without such a band, the heating required to effect a thermal bond between the tubular body 112 and the jacket 132 may cause the frayed ends of the braid to warp or bend to the point where they can penetrate through the inner layer 128 into the lumen 118 or through the thickness of the tubular stem 134.

The stem member 134 may comprise, without limitation, polyetherester elastomer, polybutylene terephthalate (PBT), or combinations thereof. Preferably, it will comprise a blend of about 90 weight percent polyetherester and about 10 weight percent polybutylene terephthalate. A desired pigment may be added as well. Additional materials that may be added include titanium dioxide, bismuth subcarbonate and iodine compounds.

Completing the catheter is a soft-tip member 140 which may be bonded to the distal end portion of the stem member 134. A suitable durometer for the soft-tip on the catheter is 30D–50D. That tip may be formed by injection molding or welding the material onto the distal end of the stem member 134. Alternatively, if the catheter is not designed to include a stem member, the soft-tip 140 may be injection molded directly onto a distal end portion of the braided tubular body 112 with an impenetrable ring 138 again being used to confine the braiding wire ends as the soft tip is being formed.

Using the above techniques, it has been possible to produce a 3 Fr O.D. catheter having a lumen with a diameter of 0.026 inches (0.066 cm) and which still possesses excellent torquing characteristics whereby the distal end of the catheter follows a rotation of its proximal end. Moreover, even with such a relatively large diameter lumen in comparison to its outer diameter, the catheter still has adequate column strength allowing it to be advanced through the vascular system without kinking or buckling. An 8 Fr diagnostic catheter constructed in accordance with the present invention may have a lumen as large as 0.086 inches (0.218 cm), again having the desirable properties expected by most cardiologists as far as its ability to be manipulated through the application of longitudinal and rotational forces at the proximal end portion of the catheter.

The reinforcing layer of the present invention, in certain embodiments, may be completely or partially embedded in either the first or second layers. In certain embodiments, it will be partially covered by both layers.

Figure 11:
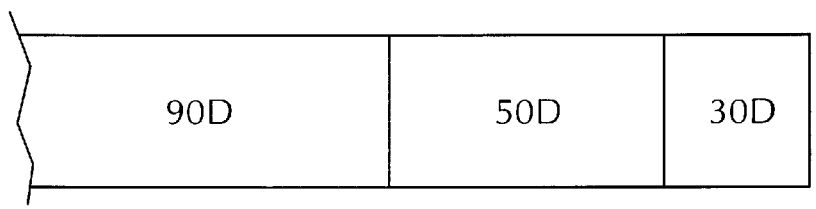
FIG. 11 is a plan view of an additional embodiment of the present invention.

FIG. 11 shows the outer layer of a distal portion of an alternative embodiment of the present invention. The distal portion is made of a polyetherester/PBT blend having a hardness of 90D, and a tip made of polyetherester having a hardness of 30D. Intermediate the 90D and 30D sections is an intermediate section made of polyetherester and having a hardness of 50D. In other embodiments, a hardness gradient will be used, so that the outer layer gradually becomes softer from the proximal to the distal direction of the distal portion.

Figure 12:
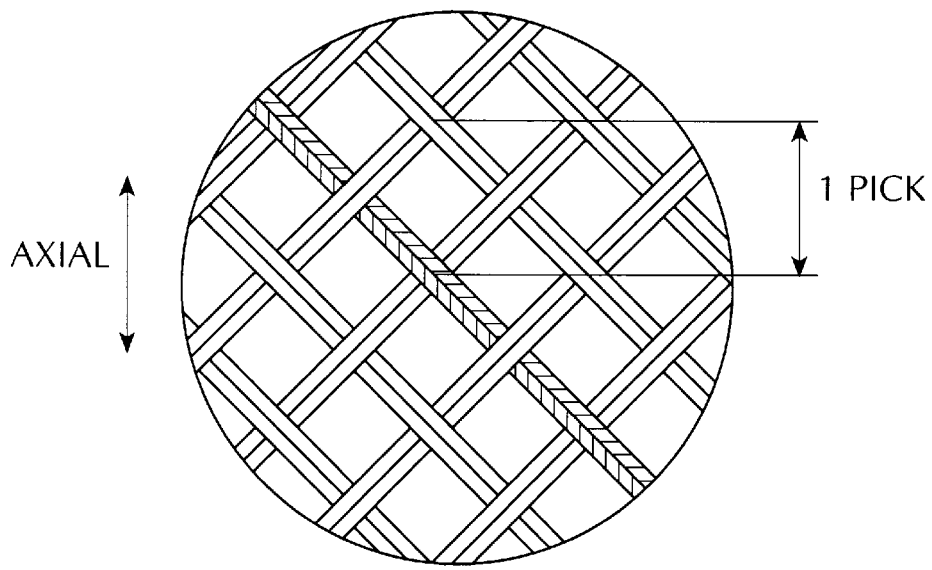
FIGS. 12 and 13 show alternative embodiments of metallic reinforcing braiding in accordance with the present invention.

FIG. 12 shows a suitable braid pattern for the reinforcing braid. Here, a 32 strand, 1-over-1, paired construction is utilized with stainless steel wire. The preferred wire diameter may be about 0.0015 to 0.0035 inches (0.0038 to 0.0089 cm), preferably about 0.0025 to 0.0030 inches (0.0064 to 0.0076 cm). Preferred braiding angles, as defined below, are between about 20–53 degrees, preferably about 30 –45 degrees. The braid illustrated in FIG. 12 would be made of a plurality of paired filaments, each pair extending in helix configuration along a center line of the braid as a common axis, the braid provided by a first number of paired filaments having a common direction of winding but axially displaced relative to each other pair and crossing a second number of paired filaments also axially disposed relative each other pair but having an opposite direction of winding. The paired wires, as shown, consist of two wires which make contact with one another along substantially their entire length, preferably along their entire length. The reinforcing braid will preferably be between about 90 and about 40 picks per inch. For a 6 Fr device, it will preferably be about 80 picks per inch, and for devices between 7–10 Fr, it will preferably be about 52 picks per inch.

Figure 13:
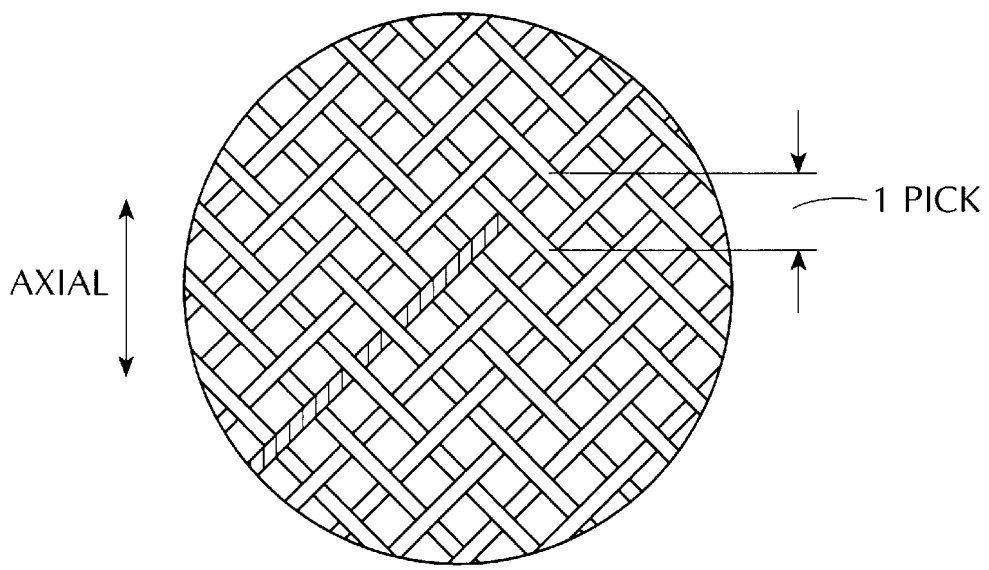

FIG. 13 shows an alternative braid pattern for the reinforcing means of the present invention. Here a 16 wire, two-over-two construction is utilized with stainless steel wire. The wire diameter may be the same as shown in FIG. 12. Preferred braiding angles are about 15–25 degrees.

Figure 14:
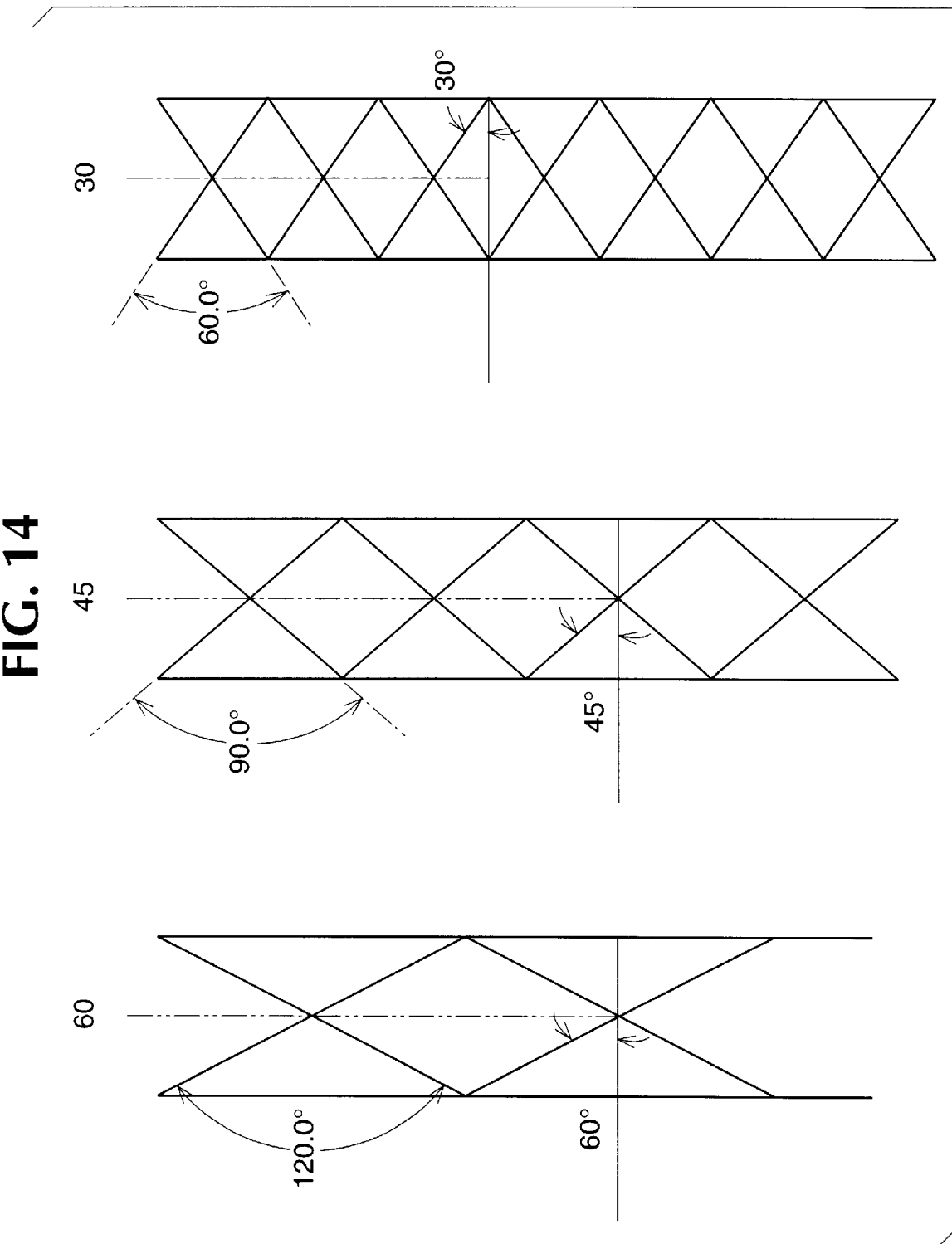
FIG. 14 shows alternative angles of braiding according to the present invention.

FIG. 14 shows alternative angles that can be used in the present invention, namely 60°, 45°, and 30°, with the braid angle measured from the place perpendicular to the longitudinal axis of the catheter. In general, radiopacity increases as braid angles decrease.

It has been found that radiopacity can be predicted based on the effective thickness of the metal braid content, and that preferred radiopacity properties are achieved with effective thickness of greater than about 0.002 inch (0.0051 cm), preferably between about 0.002 inch (0.0051 cm) and 0.0055 inch (0.0051 and 0.0140 cm), more preferably between 0.0029 and 0.0044 inch (0.0074 and 0.0112 cm).

The effective thickness can be calculated by dividing the total cross-sectional wire area by the catheter outer diameter. The total cross-sectional area of the wires can be determined in this embodiment where all wires have the same diameter and the filaments extend in a helix by calculating the area for a single wire and multiplying the result by the number of wires to yield a total cross-sectional wire area. Then, the total cross-sectional wire area is divided by the outer catheter diameter.

With reference to FIG. 15, wires 130 are braided at an angle of 30° and have diameters of 0.0030 inches (0.0076 cm). The cross-sectional area of each wire is shown as ellipses in FIG. 15, having a major diameter $d_1$ of 0.00606 inches (0.0154 cm) and a minor diameter $d_2$ of 0.003 inches (0.0076 cm). The cross-sectional area of each wire is $$\Pi\left(\frac{1}{2}d_1\right)\left(\frac{1}{2}d_2\right) = 0.0000142 \text{ inches}^2 \ (0.0000916 \text{ cm}^2).$$

The total wire cross-sectional area for all 32 wires is 0.0004544 inches$^2$ (0.002932 cm$^2$). This value is divided by the 0.105 inch (0.267 cm) diameter (D) of the catheter, to yield an effective thickness of 0.0043 inch (0.0110 cm).

Polymeric materials that may be used in the present invention are disclosed in U.S. patent application entitled "Intravascular Catheter", Ser. No. 08/647,606, filed concurrently herewith, and commonly assigned to the assignee of this application. Additional materials are disclosed in U.S. Pat. No. 5,403,292, and corresponding U.S. patent application entitled "Catheter Having Hydrophobic Properties", Ser. No. 08/343,153, filed Nov. 22, 1994, and both commonly assigned to the assignee of this application.

U.S. Pat. No. 5,403,292 relates to a diagnostic intravascular catheter having an elongated tubular body with a proximal end, a distal end and a lumen extending therebetween where the tubular body is formed with an inner layer consisting essentially of an unmodified polyamide polymer, preferably Nylon-12. The term "unmodified polyamide polymer" refers to the fact that nothing is added to the polymer matrix that tends to substantially change its physical properties, such as copolymers, polymer blends, miscible polymers in relation to polyamide-based polymer matrices or polymer performance enhancers which would substantially change the physical properties of the polymer. For instance, the fact that a colorant or a radiopaque filler material is added is not considered to be a modification. Nylon-12 is hydrophobic meaning that it does not absorb moisture and swell. Surrounding this inner layer is a reinforcing sleeve that extends from the proximal end of the tubular body toward the distal end. The sleeve may comprise braided filaments and may constrict the inner layer, creating microscopic bumps on the wall surface defining the lumen, effectively decreasing the contact area between an inserted guidewire and the wall surface. An outer layer, including a blend of a polyether block amide having a predetermined diameter hardness in the range of from about 50 Shore D to 75 Shore D and preferably a radiopaque filler material (BaSO$_4$), covers the inner layer and the reinforcing sleeve and provides an outer diameter to the tubular body in the range of from 3–8 Fr. Preferably affixed to the distal end of the tubular body member is a soft-tip member, which may be molded from a blend of resins such that the soft tip exhibits a hardness that is less than about 45 Shore D. The intravascular catheter may also incorporate a non-braided tubular stem member that is interposed between and bonded to both the tubular body and the soft-tip member. The stem member itself preferably comprises a single layer of a copolymer of polyamide and PEBA whose Shore hardness is in the range of from 25D to 72D. It may have a uniform or tapered outer diameter.

The following Table I provides a list of polymers suitable for a first layer of the present invention and provides certain properties of these polymers, as found in Polymer Structure, Properties and Applications, R. D. Deanin, Cahners Books (1972).

The following Tables II and III provide properties of certain polyetheresters suitable for a second layer of the present invention.

The following Table IV provides certain properties of polybutylene terephthalate suitable for a second layer of the present invention.

Those skilled in the art will also appreciate that the intravascular catheter in accordance with the present invention can be manufactured to have a variety of different distal end shaped configurations to suit the desires of different cardiologists. In certain embodiments, the present invention can be used in such diverse catheter applications as neurological catheters, angioplasty catheters, stent deployment devices, and the like.

Various modifications and changes in detail may be made to the above-described embodiments and examples without departing from the spirit and scope of the invention. It is therefore intended that all such matter as described in the foregoing description and shown in the attached drawings be considered as illustrative only and not limiting.

TABLE I

| Polymer | Steel on Polymer | | Polymer on Polymer | |
|---|---|---|---|---|
| | Static | Kinetic | Static | Kinetic |
| PTFE ("Teflon") (polytetrafluoroethylene) | 0.10 | 0.05 | 0.04 | 0.04 |
| PTFE-HFP copolymer (FEP "Teflon") (Tetrafluoroethylene/hexafluoropropylene) | 0.25 | 0.18 | — | — |
| Polyethylene (low density) | 0.27 | 0.26 | 0.33 | 0.33 |
| Polyethylene (high density) | 0.18 | 0.08–0.12 | 0.12 | 0.11 |
| Acetal resin ("Delrin") | 0.14 | 0.13 | — | — |
| Polyvinylidene fluoride | 0.33 | 0.25 | — | — |
| Polycarbonate | 0.60 | 0.53 | — | — |
| PET ("Mylar") (polyethylene terephthalate) | 0.29 | 0.28 | 0.27* | 0.20* |
| Nylon (polyhexamethylene adipamide) | 0.37 | 0.34 | 0.42* | 0.35* |
| PFCE ("Kel-F") (polytrifluorochloroethylene) | 0.45* | 0.33* | 0.43* | 0.32* |
| PVC (polyvinyl chloride) | 0.45* | 0.40* | 0.50* | 0.40* |
| PVDC (polyvinylidene chloride) | 0.68* | 0.45* | 0.90* | 0.52* |

*"Stick-slip" (intermittent motion).

TABLE II

| Property/Test Method | Grade 1 | Grade 2 | Grade 3 | Grade 4 | Grade 5 |
|---|---|---|---|---|---|
| Relative Viscosity/DIN 50.049–3.1.B | 3.45 ± 0.2 | 2.90 ± 0.2 | 3.20 ± 0.2 | 3.40 ± 0.2 | 2.90 ± 0.2 |
| Moisture Content/ASTM D4019 (%) | <0.025 | <0.025 | <0.025 | <0.025 | <0.025 |
| Melting Point/ASTM D2217 (° F.) | 383 | 365 | 395 | 415 | 430 |
| Hardness/ASTM D2240 (Shore D) | 38 | 45 | 55 | 63 | 74 |
| Melt Flow Index/ASTM D1238 (g/10 min.) | 25 | 40 | 10 | 7 | 4 |
| Tensile Modulus/ASTM D638 (psi) | 8,700 | 16,000 | 32,000 | 54,000 | 130,000 |
| Tensile Strength/ASTM D638 (psi) | 2,470 | 3,050 | 4,640 | 5,800 | 6,520 |
| Elongation at Break/ASTM D638 (%) | 700 | 800 | 650 | 600 | 360 |
| Flexural Modulus/ASTM D790 (%) | 7,980 | 15,000 | 29,000 | 48,500 | 117,000 |

TABLE III

| Property/Test Method | |
|---|---|
| Melt Flow Rate, 190° C. at 2.16 kg/ASTM D-1238 (g/10 min.) | 5.0 ± 1.5 |
| Melting Point/ASTM D-3418 (° C.) | 170 ± 3 |
| Specific Gravity | 1.07 ± 0.02 |
| Hardness/ASTM D2240 (Durometer) | 30 |
| Flex Modulus/ASTM D790 at 73° F. (psi) | 4000 |
| Tensile Strength at Break/ASTM D638 (psi) | 3800 |
| Elongation at Break/ASTM D638 (%) | 700 |

TABLE IV

| Property/Test Method | |
|---|---|
| Viscosity Number/ISO 1628-5 (cm$^3$/g) | 165 ± 7 |
| Volume Melt Flow Rate/ISO 1133 (cm$^3$/10 min.) | 10 ± 3 |
| Moisture Content/ASTM D4019 (wt. - %) | ≦0.05 |
| Density at 23° C./ISO 1183 (g/cm$^3$) | 1.31 ± 0.03 |
| Melting Range/DSC (° C.) | 221–226 |
| Tensile Strength at Yield/ISO 527 (N/mm$^2$) | ≧50 |
| Elongation at Yield/ISO 527 (%) | ≧3 |
| Tensile Strength at Break/ISO 527 (N/mm$^2$) | ≧30 |
| Elongation at Break/ISO 527 (%) | ≧100 |
| Modulus of Elasticity/ISO 527 (N/mm$^2$) | ≧2200 |

What is claimed is:

1. A catheter comprising an elongate tubular body having a proximal portion, a distal portion, and a lumen extending therebetween, the tubular body comprising:
    (a) a polymeric material; and
    (b) a metallic reinforcing braid comprising elongate filaments having substantially circular cross-sections, the braid having greater than 40 picks per inch and an effective thickness, calculated as total cross-sectional wire area divided by catheter outer diameter, of greater than 0.002 inches (0.0051 cm).

2. The catheter of claim 1 wherein the metallic reinforcing braid has an effective thickness of between about 0.0029 and about 0.0044 inches.

3. A catheter comprising an elongate tubular body having a proximal portion, a distal portion and a lumen extending therebetween, the tubular body comprising:
   (a) polymeric material comprising substantially no radiopaque filler; and
   (b) a metallic reinforcing braid;
   wherein the combination of polymeric material comprising substantially no radiopaque filler and metallic braid has an amount of radiopacity which is greater than or equal to the amount of radiopacity which would result from a catheter without metallic reinforcing consisting of polymeric material loaded with 20% barium sulfate.

4. The catheter of claim 3 wherein the combination of polymeric material comprising substantially no radiopaque filler and metallic braid has an amount of radiopacity which is greater than or equal to the amount of radiopacity which would result from a catheter without metallic reinforcing consisting of polymeric material loaded with 30% barium sulfate.

5. The catheter of claim 4 wherein the combination of polymeric material comprising substantially no radiopaque filler and metallic braid has an amount of radiopacity which is greater than or equal to the amount of radiopacity which would result from a catheter without metallic reinforcing consisting of polymeric material loaded with 40% barium sulfate.

6. An intravascular catheter comprising an elongate tubular body having a proximal portion, a distal portion and a lumen extending therebetween, the tubular body comprising:
   (a) a first layer defining the lumen, the first layer comprising polymeric material having a kinetic coefficient of friction (steel on polymer) of less than about 0.50;
   (b) a second layer disposed about the first layer, the second layer comprising polymeric material selected from polyetherester elastomer, polybutylene terephthalate, and combinations thereof; and
   (c) a metallic reinforcing braid comprising elongate filaments having substantially circular cross-sections, the braid having greater than 40 picks per inch and an effective thickness, calculated as total cross-sectional wire area divided by catheter outer diameter, of greater than 0.002 inches (0.0051 cm).

7. The intravascular catheter of claim 6 wherein the first layer comprises a polymer selected from the group consisting of polytetrafluoroethylene, polyvinylidene fluoride, and polyamide.

8. The intravascular catheter of claim 6 wherein the first layer comprises a polymer having a kinetic coefficient of friction (steel on polymer) less than about 0.10.

9. The intravascular catheter of claim 8 wherein the first layer consists essentially of polytetrafluoroethylene.

10. The intravascular catheter of claim 6 wherein the second layer has a durometer of from about 30D–90D.

11. The intravascular catheter of claim 6 wherein the second layer comprises polyetherester blended with polybutylene terephthalate.

12. The intravascular catheter of claim 11 wherein the second layer comprises about 10–94 weight percent polybutylene terephthalate.

13. The intravascular catheter of claim 12 wherein the second layer comprises about 8–12 weight percent polyetherester and about 88–92 weight percent polybutylene terephthalate.

14. The intravascular catheter of claim 6 wherein the metallic reinforcing braid is totally embedded between the first layer and the second layer.

15. The intravascular catheter of claim 6 wherein the metallic reinforcing braid is substantially embedded in the second layer.

16. The intravascular catheter of claim 6 wherein the metallic reinforcing braid extends from the proximal portion of the tubular body toward the distal portion of the tubular body.

17. The intravascular catheter of claim 16 wherein the metallic braid comprises metal filaments braided in a one-over-one pattern.

18. The intravascular catheter of claim 16 wherein the metallic braid comprises metal filaments braided in a two-over-two configuration.

19. The intravascular catheter of claim 16 wherein the metallic braid comprises filaments formed of a metal selected from stainless steel and ELGILOY nickel-cobalt alloy.

* * * * *